(12) United States Patent
Bland et al.

(10) Patent No.: US 10,557,788 B2
(45) Date of Patent: Feb. 11, 2020

(54) SENSOR

(71) Applicant: Aqua21 Limited, Edinburgh (GB)

(72) Inventors: Simon Bland, Edinburgh (GB); Trevor Costello, Edinburgh (GB)

(73) Assignee: Aqua21 Limited, Edinburgh (GB)

( * ) Notice: Subject to any disclaimer, the term of this patent is extended or adjusted under 35 U.S.C. 154(b) by 0 days.

(21) Appl. No.: 15/736,521

(22) PCT Filed: Jun. 17, 2016

(86) PCT No.: PCT/GB2016/051822
§ 371 (c)(1),
(2) Date: Dec. 14, 2017

(87) PCT Pub. No.: WO2016/203259
PCT Pub. Date: Dec. 22, 2016

(65) Prior Publication Data
US 2018/0356336 A1    Dec. 13, 2018

(30) Foreign Application Priority Data

Jun. 19, 2015 (GB) .................................. 1510851.7

(51) Int. Cl.
*G01N 21/25* (2006.01)
*G01N 21/33* (2006.01)
(Continued)

(52) U.S. Cl.
CPC ......... *G01N 21/33* (2013.01); *G01N 21/8507* (2013.01); *G01N 33/1893* (2013.01)

(58) Field of Classification Search
CPC .... G01N 21/00; G01N 21/33; G01N 21/8507; G01N 33/18; G01N 33/50; G01N 15/02; A61L 2/24; B01D 46/00; B01D 46/46
See application file for complete search history.

(56) References Cited

U.S. PATENT DOCUMENTS

| 4,619,530 A | 10/1986 | Meserol et al. |
| 2002/0080349 A1* | 6/2002 | Armstrong ....... G01N 27/44721 356/246 |

(Continued)

FOREIGN PATENT DOCUMENTS

| CN | 101504371 A | 8/2009 |
| CN | 201935868 U | 8/2011 |

(Continued)

OTHER PUBLICATIONS

International Search Report and Written Opinion for counterpart PCT Application No. PCT/GB2016/051822, dated Feb. 1, 2017 (23 pgs.).

*Primary Examiner* — Abdullahi Nur
(74) *Attorney, Agent, or Firm* — Shumaker & Sieffert, P.A.

(57) ABSTRACT

In the field of substance detection an apparatus can be provided for detecting the concentration of a substance in a fluid that allows detection of a substance to be made in situ, in real time. In some examples the apparatus includes a transparent housing arranged to contain the fluid, a source operable to generate and direct light through the housing containing the fluid, wherein the housing is operable to focus light passing therethrough; and a detector operable to detect the intensity of light transmitted through the housing.

37 Claims, 8 Drawing Sheets

(51) Int. Cl.
*G01N 33/18* (2006.01)
*G01N 21/85* (2006.01)

(56) References Cited

U.S. PATENT DOCUMENTS

| | | | |
|---|---|---|---|
| 2003/0140712 A1* | 7/2003 | Barger | G01F 1/8404 |
| | | | 73/861.354 |
| 2013/0316934 A1 | 11/2013 | Matayoshi et al. | |
| 2015/0330955 A1* | 11/2015 | Farnsworth | G01N 30/74 |
| | | | 250/373 |

FOREIGN PATENT DOCUMENTS

| | | |
|---|---|---|
| CN | 202886287 U | 4/2013 |
| CN | 203772733 U | 8/2014 |
| EP | 0115902 A2 | 8/1984 |
| EP | 0653620 A1 | 5/1995 |
| EP | 2607883 A1 | 6/2013 |
| JP | 6212841 A | 1/1987 |
| JP | 6222026 A | 1/1987 |
| JP | 2013148518 A | 8/2013 |
| JP | 2014137319 A | 7/2014 |

\* cited by examiner

SENSOR

This application is a U.S. national phase application under 37 U.S.C. § 371 of International Application No. PCT/GB2016/051822 filed on Jun. 17, 2016, which claims priority to GB Application No. 1510851.7 filed Jun. 19, 2015. The entire contents of each of PCT/GB2016/051822 and GB Application No. 1510851.7 are incorporated herein by reference.

TECHNICAL FIELD

The present disclosure relates to the field of substance detection in fluids and in particular but not exclusively to an apparatus and method for detecting ozone in water.

BACKGROUND

Purification of fluids and in particular of water supplies is a long established field. For example it has been identified that water contaminated with, for example bacteria or viruses, can assist in the spread of water borne diseases. Additionally some substances, e.g. lead, are poisonous if consumed. Water can therefore be treated to remove harmful substances before it is consumed or used in order to assist in the prevention of disease.

There are a number of methods of removing unwanted or harmful substances from water. These include the performance of full- or part-sterilisation of the water to kill, denature or otherwise harm biological contaminants, for example bacteria. The addition of substances can also be performed to react with water-born chemical contaminants so as to transform these into removable or less harmful forms. Examples of approaches to sterilisation include the addition of chemicals such as chlorine or ozone, or the treatment of water with ultraviolet light. Examples of approaches to remove harmful substances by way of chemical reaction include the addition of water softeners, such as ion exchange resins, to remove chemicals such as ferrous iron, calcium and magnesium by ion exchange.

The use of ozone in water treatment is known to provide effective removal of unwanted substances in some applications. Ozone is a highly reactive molecule which readily reacts with a number of substances including biological substances such as viruses, bacteria, protozoa etc. Ozone treatment can also be expected to result in a lower risk of creating dangerous by-products than other methods such as the addition of chlorine. It has been established that a residual ozone concentration of 0.07 parts per million present for at least 1 second implies water fit for consumption. Thus in establishing a reliable ozone purification approach it may be of utility to detect the concentration of ozone present in the water.

Existing methods of detecting the presence and concentration of ozone in water include chemical titration, separation of ozone from water using a membrane then reacting this with a catalyst and using electrochemistry to monitor the products, and monitoring the absorption of UV light by ozone in water.

The first two of these methods require that the water be removed from a system and tested before the ozone concentration can be detected. Detection of the concentration of ozone is therefore delayed until the relevant tests and reactions have been carried out, during which time the water may need to be stored before it is confirmed that it is safe to distribute.

Additionally, these methods may require frequent sampling and associated testing, which may require a high degree of human input for all of the accessing water for sampling, sampling and testing.

Monitoring the absorption of UV light is used in large industrial ozone plants. Very few other gases absorb light as strongly as ozone in the deep UV frequencies and thus the use of UV light can provide a reliable ozone detection method. This method can also provide results rapidly, for example without having to wait for results of chemical reactions. However UV based ozone detectors are typically very large and very expensive. UV based ozone detectors typically have low portability due to the use of UV discharge lamps that require careful handling. Such discharge lamps may also have a limited life span and therefore require regular replacement, bringing therewith associated cost and human input.

Known approaches for measuring the concentration of a substance in a fluid are described in US2003025909A, US2008304048A, JP2001056292A, JP2002005826A, JP200306592A, JP2003329585A, JP2011169875A, JP3131741A, JP3223726B, RU143323U and RU44181U.

SUMMARY

Particular and preferred aspects are set out in the accompanying claims.

Viewed from a first aspect there is provided an apparatus for detecting the concentration of a substance in a fluid. The apparatus includes a housing arranged to contain the fluid, a source operable to generate and direct light through the housing, wherein the housing is configured to focus light passing therethrough; and a detector operable to detect the intensity of light transmitted through the housing.

Viewed from a second aspect there is provided a method of detecting a concentration of a substance in a fluid. The method includes: directing light from a source through a housing containing fluid, wherein the housing is arranged to focus the light passing therethrough; and detecting an intensity of light transmitted through the housing.

Viewed from a third aspect there is provided an apparatus for in-system control of a concentration of a substance in a fluid. The apparatus including a sensor of the type described above arranged to detect a substance concentration of the system; a comparator arranged to compare a detected substance concentration with a target substance concentration; and a concentration modifier arranged to alter the concentration of the substance in the system when a detected substance concentration does not match the target substance concentration.

Viewed from a fourth aspect there is provided a method of controlling a substance concentration in system. The method including detecting a substance concentration in the system according to the method described above; comparing the detected substance concentration with a target substance concentration; and controlling a concentration modifier to alter the substance concentration when the detected substance concentration does not match the target substance concentration.

Further feature combinations provided by the present teachings will be understood from the following detailed description and accompanying figures.

BRIEF DESCRIPTION OF DRAWINGS

The present teachings will now be described by way of example only with reference to the following drawings in which like numerals reflect like elements.

Figure 1:
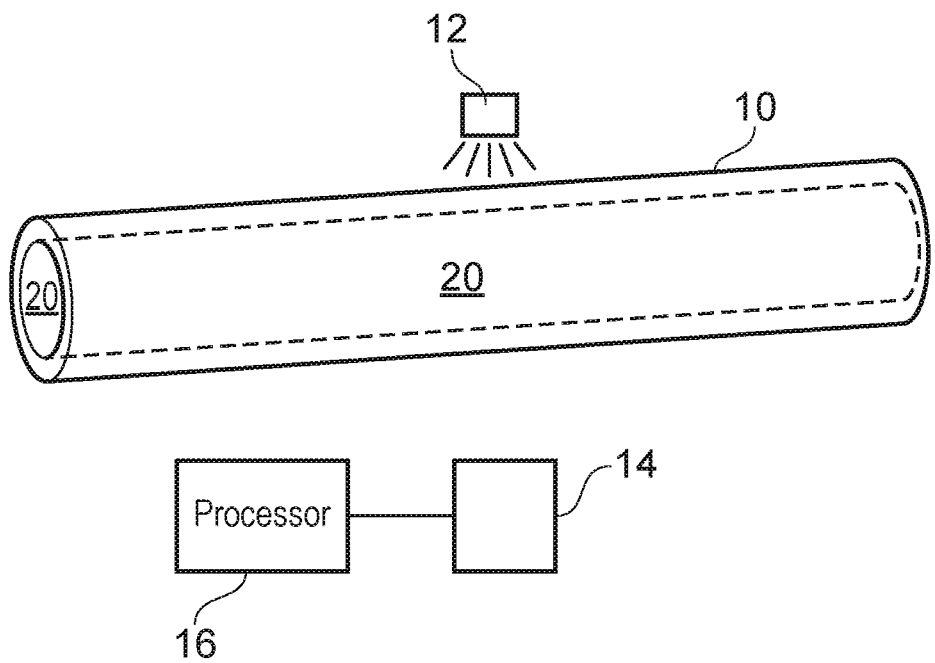
FIG. 1 illustrates a schematic illustration of a sensor.

While the present teachings are susceptible to various modifications and alternative forms, specific embodiments are shown by way of example in the drawings and are herein described in detail. It should be understood however, that the drawings and detailed description attached hereto are not intended to limit the teachings to the particular forms disclosed but rather the scope afforded is to cover all modifications, equivalents and alternatives falling within the spirit and scope of the appended claims.

DETAILED DESCRIPTION

Fluid is commonly communicated from one location to another in conduits such as pipes. The sensor of the present disclosure has utility in detecting a substance in a fluid as it flows through a pipe.

With reference to FIGS. 1-4, a first example apparatus for detecting a substance in a fluid as the fluid flows through a pipe will be described in the context of a system configured to detect ozone concentration in water.

FIG. 1 illustrates a sensor for sensing the concentration of ozone in water. Water 20 is contained within a pipe or tube 10. In the present example the pipe 10 is a pipe section that can be connected at either end to pipes of a water system. Thus the water system is unmodified in its water transportation function whilst also providing an ozone sensing capability. Thus from one perspective the pipe 10 acts as a housing for the water from the point of view of the ozone sensor, while acting as a pipe from the point of view of water transportation.

The pipe 10 of the present example is formed of a material that is transparent to ultra violet (UV) light having a wavelength suited to detection of ozone in water. Accordingly in the present example, the material is transparent to UV light having a wavelength of 253-267 nm. In one example, the material is transparent to UV light at a particular wavelength of 255 nm. In particular the pipe 10 is formed of a material that has a high transmission of UV light i.e. the material has a high transparency to UV light. In the present disclosure a high transparency is considered to be 90% transmission at the relevant wavelength. In the present example quartz is used as it provides a transparency of 90-95% transmission to UV light in the wavelength range suited for ozone detection (in contrast to glass which has a low transmission of only 50% in the relevant wavelength range) and has sufficient strength to function as a pipe section in the water system. Other materials having the required transparency and strength may also be used.

A light source 12 is provided on one side of the pipe 10 and oriented so as to direct UV light output by the source into the pipe 10. In the present example the light source is a UV light emitting diode (LED). In the present example the UV LED used is a UV LED in the UVTOP™ range manufactured by Sensor Electronic Technology Inc. and which is configured to emit light of between 250-265 nm. In another example, other UV LED sources may be used. In further examples the light source 12 may be a laser source. The light source 12 may thus be any light source suitable for generating UV light.

A detector 14 is provided on an opposite side of the pipe 10 to the light source 12. In this manner the light source 12 and detector 14 are arranged such that light is transmitted from the light source 12 through the pipe 10 onto the detector 14 on the opposite side of the pipe 10. The detector 14 may be any detector suitable for detecting UV light for example a photodiode. The detector may include any photosensitive element that produces a signal responsive to the intensity of light received. In the present example a Det10a biased Si photodiode manufactured by Thorlabs inc. or a FDS010 photodiode, also manufactured by Thorlabs Inc. is used. The detector 14 is connected to a processor 16 that is configured to process the output signal from the detector 14.

In order to efficiently utilise the light from the sensor, the apparatus of the present example focusses the light through the pipe 10 towards the detector 14. In particular, the curved surface of the pipe 10 provides a focussing effect to concentrate light entering the pipe 10 in the direction of the detector 14. Thus the present example provides that as UV light enters the pipe 10 it is focused by the curved surface of the quartz material of the pipe 10 and thereby provides that sufficient light arrives at the detector 14 to facilitate use of a relatively inexpensive detector 14 whilst maintaining that the detector output signal is in normal use above the noise floor. The transparent pipe 10 thus acts as a cylindrical lens as shown in more detail in FIG. 2.

Figure 2:
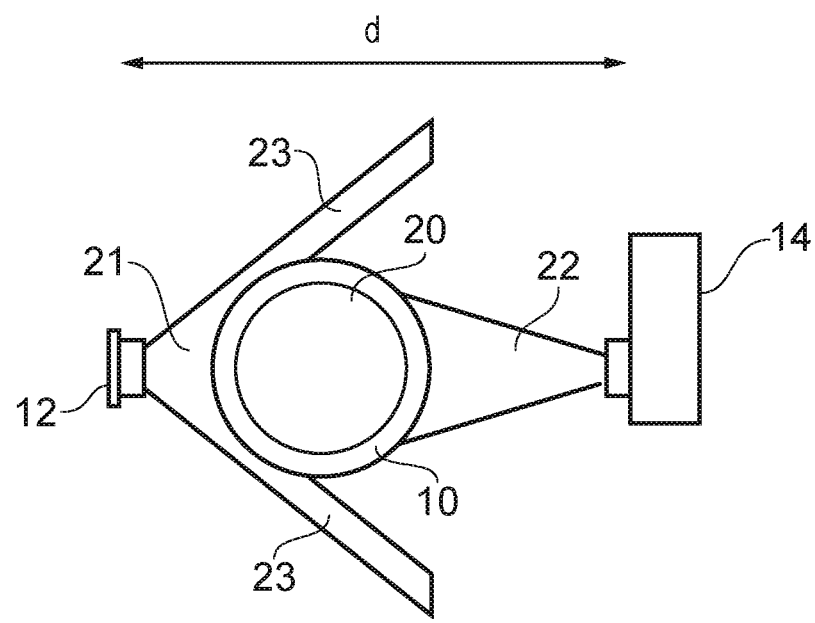
FIG. 2 illustrates an end view of the sensor illustrated in FIG. 1.

FIG. 2 illustrates an end view of the detector illustrated in FIG. 1. As discussed above the pipe 10 acts as a cylindrical lens thereby focussing the light towards the detector 14 as it enters the pipe. This provides convergent focus of the light such that the light rays 21 emitted from the source 12 are focused as they enter the pipe 10 in the direction of the detector 14. As shown in the illustrated example, the pipe also acts as a cylindrical lens as the light rays 22 exit the pipe 10 towards the detector 14. The cylindrical surface of the quartz material of the pipe 10 focuses the light rays 22 as they exit the pipe 10 towards the detector 14. The focal length of the cylindrical lens formed of the pipe and the fluid contained therein depends on the material of the pipe and the fluid contained therein. In the present example, water has similar refractive properties to quartz and thus the pipe containing water acts as a solid quartz rod. In order for light to be focussed onto the detector the distance between the source 12 and the detector 14 is greater than the focal length of the pipe.

In the present example the only focussing element is provided by the pipe. However in some examples additional focussing elements e.g. additional lenses, are provided between the UV LED and the pipe in order to focus the light before it enters the housing. In one example a UV LED containing a hemispherical lens is used. In other examples a separate lens is provided between the LED and the pipe.

As seen in FIG. 2, the source 12 is arranged such that the cone angle of emitted light causes some light rays 23 emitted to miss the pipe 10. The detector 14 is arranged such that the cone angle of detection is narrower than the cone angle of emission such that only light that has passed through the pipe 10 is detected. Thus the amount of light received by the detector 14 is not the same as the amount of light emitted from the source 12, even if no light absorption takes place due to a fluid in the pipe or the material of the pipe. In the present example the amount of light detected is sufficient to enable the presence of ozone to be detected. However in certain other examples the cone angle of emission is selected to ensure that all the light emitted by the source 12 passes through the pipe and is directed onto the detector 14. In the present example light emitted from the LED has a cone angle of approximately 60 degrees and so almost all light enters the pipe thereby resulting in minimal loss of light to the atmosphere.

Figure 3:
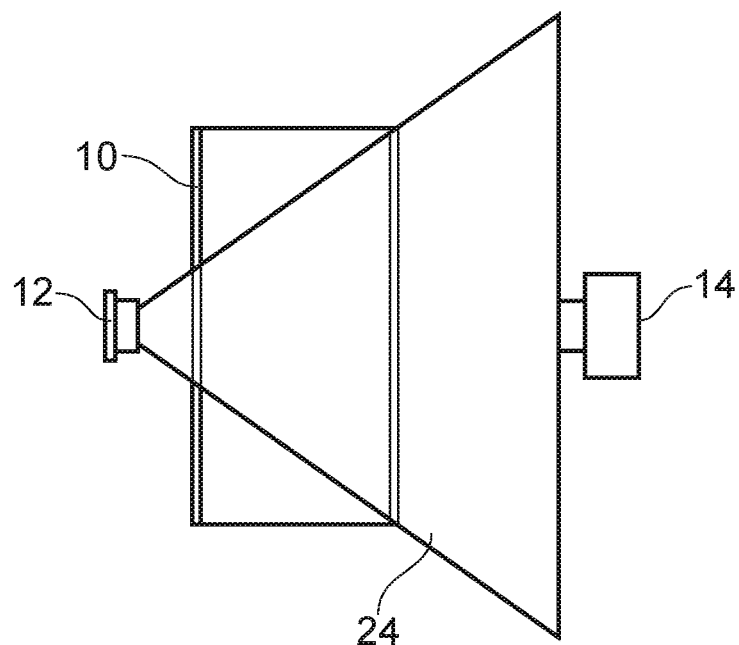
FIG. 3 illustrates a top view of the sensor illustrated in FIG. 1.

FIG. 3 is a top view of the sensor illustrated in FIG. 1. As can be clearly seen, in the present example light 24 is not focussed by the pipe 10 along its axial length since the pipe 10 does not change shape along its length. Thus UV light from the source is only focused in one dimension. Viewed from another perspective, light is focused when it meets the pipe 10 at a curved surface of the pipe 10, for example when light is directed towards the outer edge of the circular cross section of the pipe 10 when viewed from the end as illustrated in FIG. 2. However light is not focused when it meets the pipe 10 at a constant surface of the pipe for example when light is directed towards the outer edge of the rectangular cross section of the pipe 10 when viewed from above as illustrated in FIG. 3. If focus in the longitudinal dimension of the pipe 10 is required, for example to provide that a greater proportion of the emitted light energy is focussed toward the detector 14, then an additional focussing element is provided between the source and the pipe to provide focus in that second dimension.

In some examples, the components of the sensor are housed in a container 40 such that the sensor is contained within a small robust package that protects the sensor from damage. The container 40 of the present example is formed of acrylonitrile butadiene styrene however other materials such as other plastics or metals may also be used. In the present example the container 40 is manufactured by 3D printing.

Figure 4A:
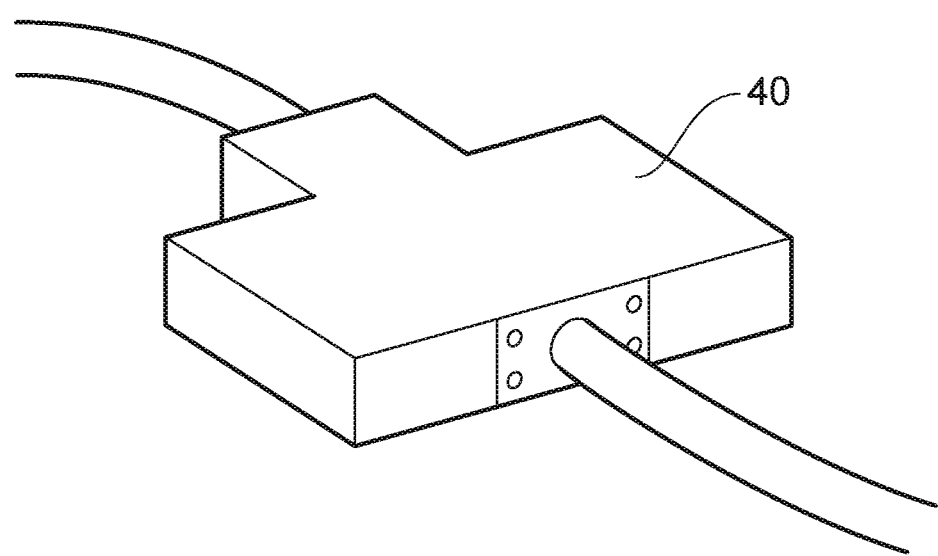
FIG. 4A illustrates a container for the sensor illustrated in FIG. 1.
Figure 4B:
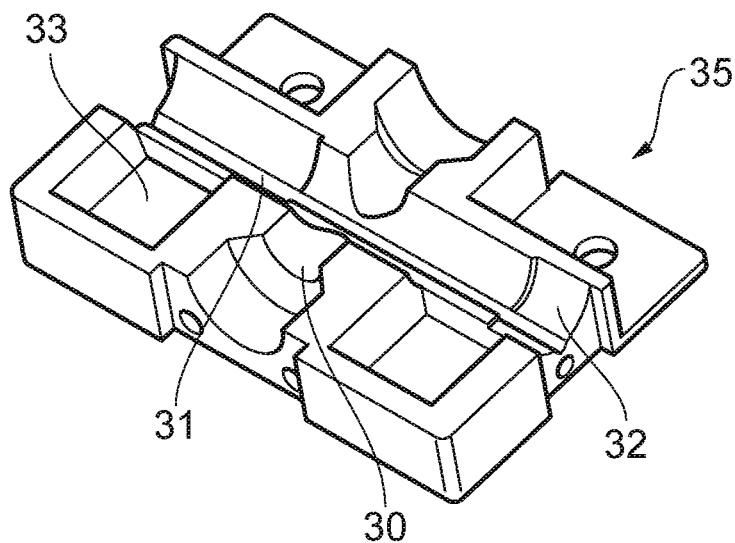
FIG. 4B illustrates an internal structure located in the container illustrated in FIG. 4A.

FIG. 4A illustrates the outside of such a container 40 and FIG. 4B illustrates the inside of such a container 40. Inside the container 40 is a structure 35 arranged to provide support to each of the components of the sensor. Pipe 10 is supported by a support structure 30 arranged to fit around the outside of the pipe 10. The support structure 30 is a curved surface having an inner shape that corresponds to the outer shape of pipe 10. In this manner the curved surface is arranged to support the pipe 10 in position. The structure 35 also includes structures to support or locate the source 12, detector 14 and processor 16 in position. The source 12 is located in a source supporting location 31, the detector 14 is located in a detector supporting location 32 and the processor 16 is located at a processor supporting location 33. The inner shape of the structure 35 is shaped at each location to correspond to the shape of the relevant component thereby providing support and positioning the component in the correct location. In some examples the processor 16 is not located in the container 40. Instead a connector is provided in the container 40 arranged to connect the detector 14 to a processor located outside of the container 40. In such an example the connector is located on a connector mount arranged on the inner structure 35 of the container 40.

The detector 14 therefore detects light once it has passed through the pipe 10 and provides an output signal related to the intensity of light received by the detector 14. The output signal may be directly proportional to the amount of light received by the detector 14 i.e. the more light detected, the greater the output signal. Alternatively the output signal may be inversely proportional to the amount of light received by the detector 14 i.e. the more light detected, the lower the output signal. In some examples the relationship between the light detected and the intensity of the light may follow a specific response curve. The output signal from the detector 14 can then be used by the processor 16 to determine the concentration of ozone in the water in the pipe 10.

The concentration is determined using Beer-Lambert law which states that $$C = \left(\frac{1}{(\sigma L)}\right) \ln\left(\frac{I_0}{I}\right) \quad \text{(Equation 1)}$$

In which C is the concentration, $I_0$ is the intensity of light measured with no ozone present, I is the intensity of light measured with ozone present, L is the path length and σ is the absorption cross section at the probing wavelength. In the present example σ is $1.15 \times 10^{-17}$ $cm^2$ $molecule^{-1}$ at a wavelength of 254 nm.

The path length L is the distance d between the light source 12 and the detector 14 and is set in advance of operation based on the wavelength of light used and the substance being detected. In the present example of detecting ozone, UV light with a wavelength of 250-265 nm is used and the distance is set to 30 mm.

In order to prove that the sensor described above detects ozone as well as known sensors that detect the presence of ozone based upon sampling and chemical testing of the water, the inventors carried out an experiment in which the sensor described above was compared with a known membrane sensor.

A sensor formed of a UV LED and photodiode of the type described with reference to FIGS. 1-4 was used to monitor input water. This monitoring took place when the input water was flowing through a fused quartz tube. A second UV LED and photodiode of the type described with reference to FIGS. 1-4 was used to monitor ozonated water flowing through a second fused quartz tube. The quartz tubes had an outer diameter of 8 mm and an inner diameter of 6 mm. Each of the LEDs emitted light into a large wide angle cone with a half viewing angle of approximately 60 degrees. In operation the LEDs were powered at 6V, 30 mA.

An ozone generator of the type described in International Patent Application WO2013/030559 was arranged to introduce ozone to the water flowing through the second quartz tube. The ozone generator was switched on to introduce ozone into the water at 120 seconds and was switched off at 300 seconds. Finally a calibrated membrane based sensor was arranged in series with the second UV LED and photodiode such that the results of the detector described with reference to FIGS. 1-4 could be compared with a known detector.

Figure 5:
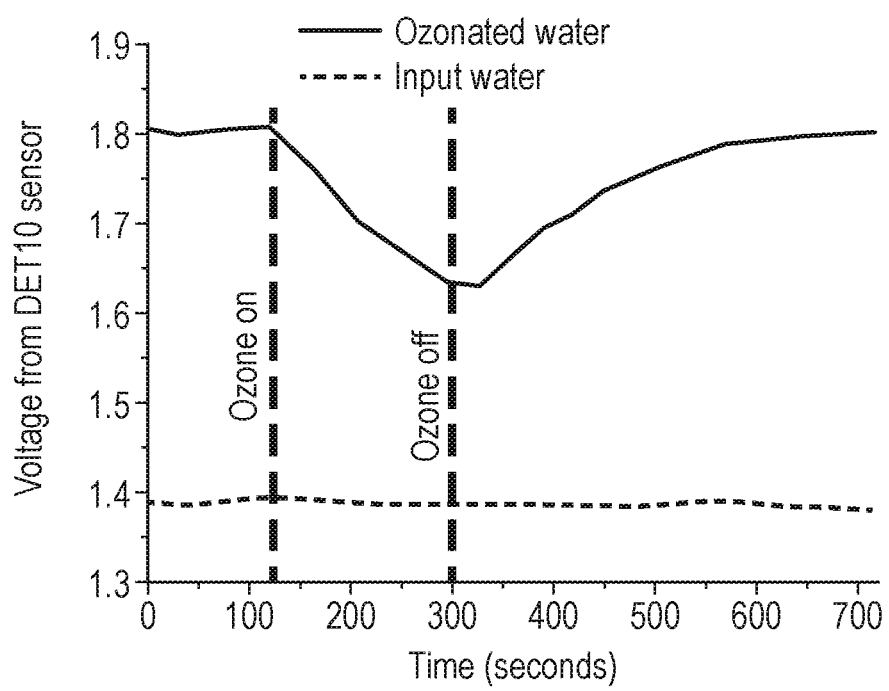
FIG. 5 is a graph illustrating the effect of ozone on the output signal of the sensor illustrated in FIG. 1.

FIG. 5 illustrates the results of the experiment and the effect of a change in the concentration of ozone on the voltage of the photodiodes. As can be seen in the graph of FIG. 5, the dashed line (labelled "input water") having a value of just under 1.4 indicates the signal output by the first photodiode arranged to monitor water in the first quartz tube i.e. water that has not been ozonated. The solid line (labelled "ozonated water") having a value ranging from 1.8 to 1.65 indicates the voltage of the second photodiode arranged to monitor the water flowing through the quartz tube downstream of the ozone generator.

The output signal of the first photodiode is lower than the output signal of the second photodiode. This is due to an offset in the output of the first photodiode and thus the signal obtained from the sensor arranged to monitor the voltage across the fluid in the second quartz tube is higher than the signal obtained from the sensor arranged to monitor the voltage across the fluid in the first quartz tube.

As clearly shown by the graph of FIG. 5, the introduction of ozone to the water flowing through the second quartz tube resulted in a drop in the output signal of the second photodiode. This is due to ozone's strong absorption of deep UV light. Conversely when the ozone generator was switched off the voltage increased back to its original level prior to the introduction of ozone as the ozonated water flowed through the quartz tube and away from the second photodiode.

Figure 6:
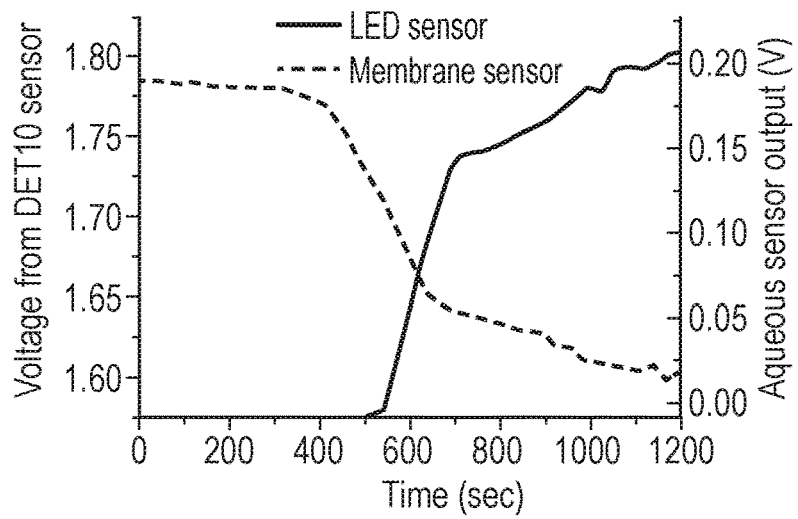
FIG. 6 is a graph illustrating the output signal of the sensor illustrated in FIG. 1 and the ozone concentration measured by a membrane based ozone sensor during a first experiment

Tests were also made using the conventional calibrated membrane based ozone sensor and the two sets of results were compared. FIG. 6 illustrates the results of the first test which was performed at 17.5 degrees centigrade, with a flow rate of 0.73 litres/minute. The solid line illustrates the signal output by the second photodiode (labelled "LED sensor") and the dashed line illustrates the signal output by the conventional calibrated membrane based sensor (labelled "membrane sensor"). The ozone generator was switched on at 240 seconds.

As can be seen from FIG. 6, the increase in signal of the membrane based sensor corresponded with the reduction in signal output from the second photodiode, although the membrane based sensor signal lagged behind the photodiode signal by approximately 60 seconds. This was due to the membrane sensor taking longer to react to the presence of ozone and the time taken for the level of ozone to build up in the water in which the membrane based sensor was submerged in.

Figure 7:
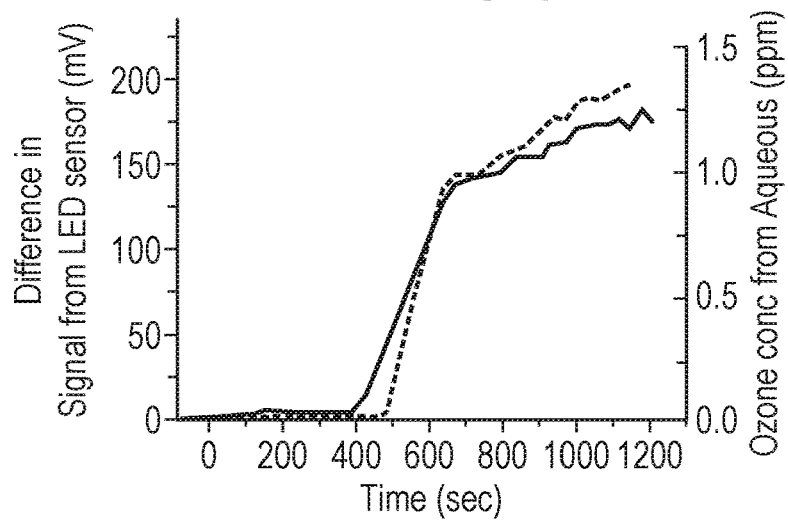
FIG. 7 is a graph illustrating the difference signal of the sensor illustrated in FIG. 1 and the ozone concentration measured by a membrane based ozone sensor during a first experiment.

FIG. 7 illustrates the results of FIG. 6 after the membrane based sensor signals have been calibrated and shifted by 60 seconds (shown by the dashed line). In FIG. 7 these have been plotted against the difference in signal of the second photodiode (shown by the solid line). It can be seen that the reduction in signal measured by the second photodiode closely follows the ozone concentration measured by the membrane based sensor. Therefore in its simplest form the following linear relationship could be used:

$$C = V_{diff} \times 0.007 \quad \text{(Equation 2)}$$

In which C is the concentration of ozone calculated using the signals output from the UV LED based sensor in parts per million, $V_{diff}$ is the difference in voltage from the photodiode in mV, and 0.007 is a constant.

Figure 8:
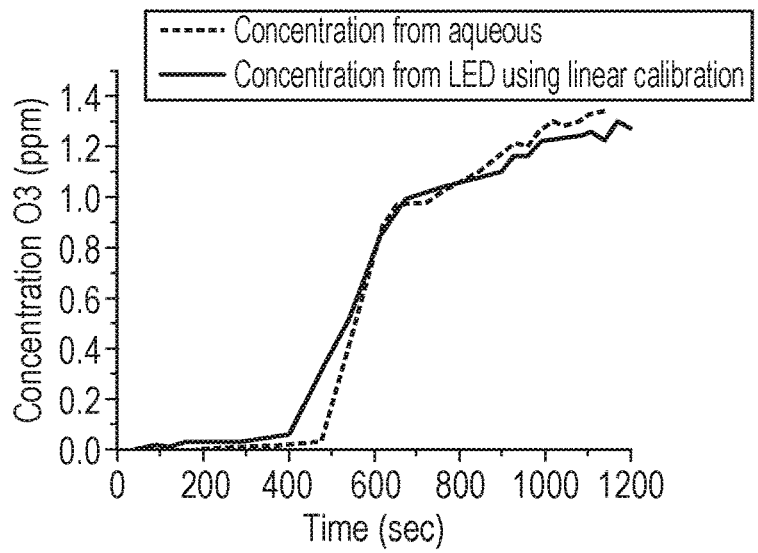
FIG. 8 is a graph illustrating the ozone concentration calculated from the output signals from the sensor illustrated in FIG. 1 using a simple linear relation and the ozone concentration measured by a membrane based ozone sensor during a first experiment.

FIG. 8 illustrates the comparison between the concentration detected by the membrane-based detector indicated by the dashed line (labelled "concentration from aqueous") with the concentration calculated using Equation 2 using the signals output from the UV LED based sensor indicated by the solid line (labelled "concentration from LED using linear calibration"). A good correlation between the concentrations obtained from the two different sensors can be seen.

A disadvantage of using Equation 2 to calculate the concentration of ozone is its sensitivity to the initial light intensity which could easily change between experiments for example due to any small alteration in alignment of the sensor, the level of pollution in the water etc. A more rigorous approach using Beer Lambert law results in the following equation:

$$C = 12 \times \ln\left(\frac{V_I}{V_m}\right) \quad \text{(Equation 3)}$$

In which C is the concentration of ozone in parts per million calculated using the signals output from the UV LED based sensor, $V_I$ is the initial voltage at time t=0 seconds by the second photodiode and $V_m$ is the voltage measured by the second photodiode when time t is greater than 0 seconds.

Figure 9:
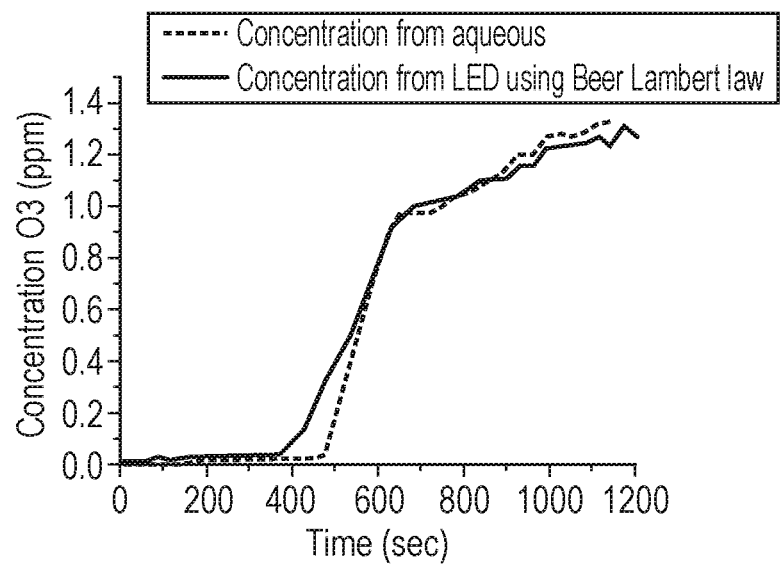
FIG. 9 is a graph illustrating the ozone concentration calculated from the output signals from the sensor illustrated in FIG. 1 using Beer Lambert Law and the ozone concentration measured by a membrane based ozone sensor during a first experiment.

FIG. 9 illustrates the comparison between the concentration detected by the membrane-based detector with the concentration calculated using Equation 3 using the results from the UV LED based sensor. The solid line labelled "concentration from aqueous" illustrates the concentration detected by the membrane-based sensor and the dashed line labelled "concentration from LED using Beer Lambert law" illustrates the concentration calculated using Equation 3 and the results of the UV LED based sensor. Once again the graph illustrated in FIG. 9 shows a good correlation between the concentrations calculated using the signals output from the UV LED based sensor and the concentrations measured by the membrane-based sensor. When comparing FIG. 9 and FIG. 8 it can be seen that the use of Equation 3 leads to improved accuracy in particular at later times.

Figure 10:
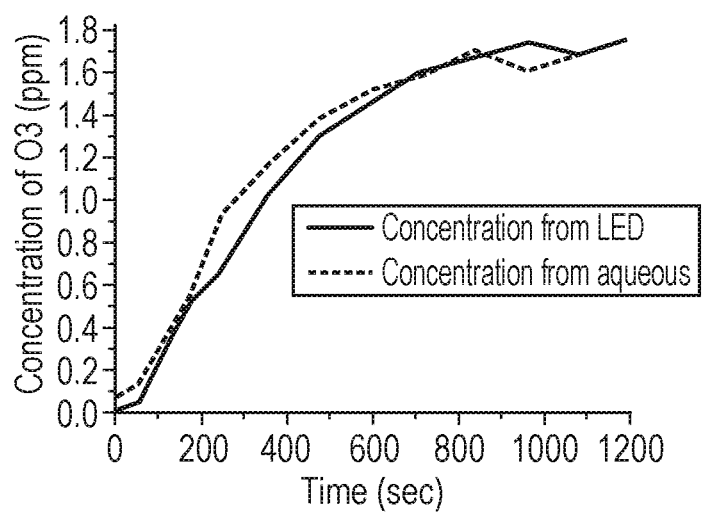
FIG. 10 is a graph illustrating the ozone concentration calculated from the output signals from the sensor illustrated in FIG. 1 using Beer Lambert Law and the ozone concentration measured by a membrane based ozone sensor during a second experiment.

In order to test the accuracy and repeatability of the use of a UV LED based sensor and the calculation of concentration using Equation 3, a second experiment was performed. The results of this experiment are shown in FIG. 10 in which the concentration of ozone calculated using Equation 3 from the signals obtained from the UV LED based detector (shown by the solid line labelled "concentration from LED") has been plotted against the concentration measured by the membrane based sensor (shown by the dashed line labelled "concentration from aqueous"). Once again a good correlation between the results of the two sensors can be seen.

It has therefore been demonstrated that a sensor of the type described with reference to FIGS. 1-4 is able to detect the concentration of ozone with a similar accuracy to a known membrane based detector. As is also clear from the results presented above, the sensor of the present disclosure operates with a lower time lag than the conventional membrane sensor and thus provides the relevant information quickly in real time. The sensor of the present disclosure therefore provides a cost effective and easy to manufacture sensor contained in a compact housing. By using LED technology, the sensor is more energy efficient than conventional sensors and thus provides advantages in terms of power consumption. The sensor of the present disclosure also provides the additional advantage of facilitating installation, particularly in remote locations, due to its compact size and shape. Since the sensor of the present disclosure is arranged to monitor the concentration of ozone in water in real time as it passes the sensor, in situ detection of ozone in water is possible.

Figure 11:
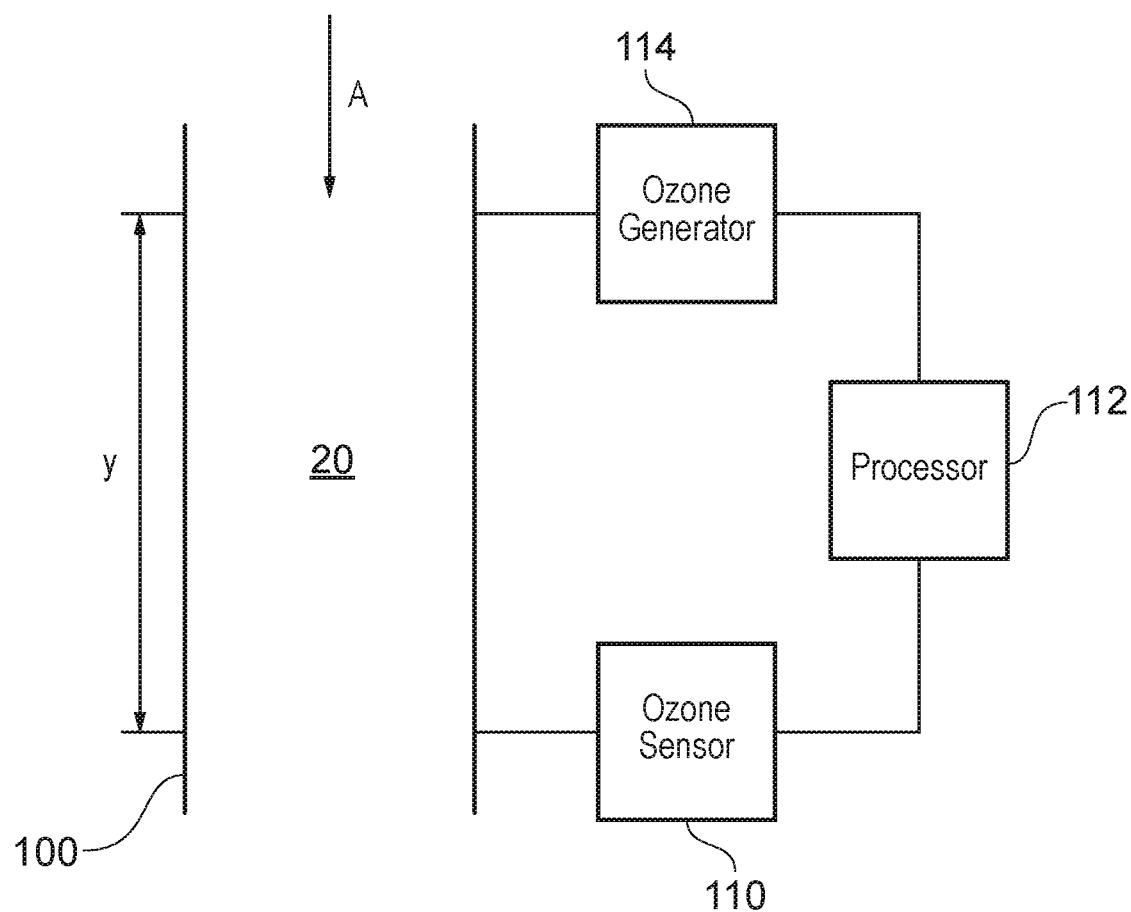
FIG. 11 illustrates a water purification system including the sensor illustrated in FIG. 1.

One example in which in situ detection of ozone in water may be useful is in a water purification system. FIG. 11 illustrates a sensor of the type described with respect to FIGS. 1-4 in use in a water purification system. Water 20 flows through a pipe 100 in the water purification system in the direction of arrow A. An ozone generator 114 is arranged to introduce ozone into the water as it flows through the pipe 100. As such the ozone generator may be considered to be an ozone concentration modifier or adjuster. An ozone sensor 110 is arranged downstream of the ozone generator 114 in order to detect the concentration of ozone in the water 20 as it flows past. The ozone sensor 110 is a sensor of the type described above with respect to FIGS. 1-4. The ozone generator may be any ozone generator but in the present example is an ozone generator of the type described in International Patent Application WO2013/030559. A processor 112 is connected to the ozone sensor 110 and the ozone generator 114 and is configured to control the ozone generator 114 based on the output from the ozone sensor 110. In some examples the processor may be in a different location to the sensor and may control the sensor using wireless technology.

As mentioned above, one accepted measure of whether ozonation has achieved sufficient purification of water is that a suitable concentration of ozone has been present in the water for a suitable length of time. In one example, the concentration is 0.07 parts per million (ppm) and the length of time is at least one second. The water purification system of the present example therefore provides for measuring both an ozone concentration in the water and an exposure time at that concentration.

The ozone generator 114 is located a distance y upstream of the ozone sensor 110. The distance y is calculated using the flow rate of water through the system such that the ozone generator is located a set distance from the ozone sensor. In the present example distance y is calculated such that the time taken for the water to travel distance y from the ozone generator 114 to the ozone sensor 110 is 1 second. Since it is known that an ozone concentration of 0.07 ppm present for 1 second is sufficient for an acceptable level of water purification to have been achieved, if the ozone sensor detects that the concentration of ozone matches 0.07 ppm, then it can be assumed that the water has reached an acceptable state of purification.

This is because the ozone concentration cannot have changed between the ozone generator and the ozone sensor and the length of time for the water to travel this distance is sufficient to result in an acceptable level of water purification. Thus the water purification system of the present example can be operated to provide an acceptable level of confidence that ensures sufficient water purification has occurred.

Figure 12:
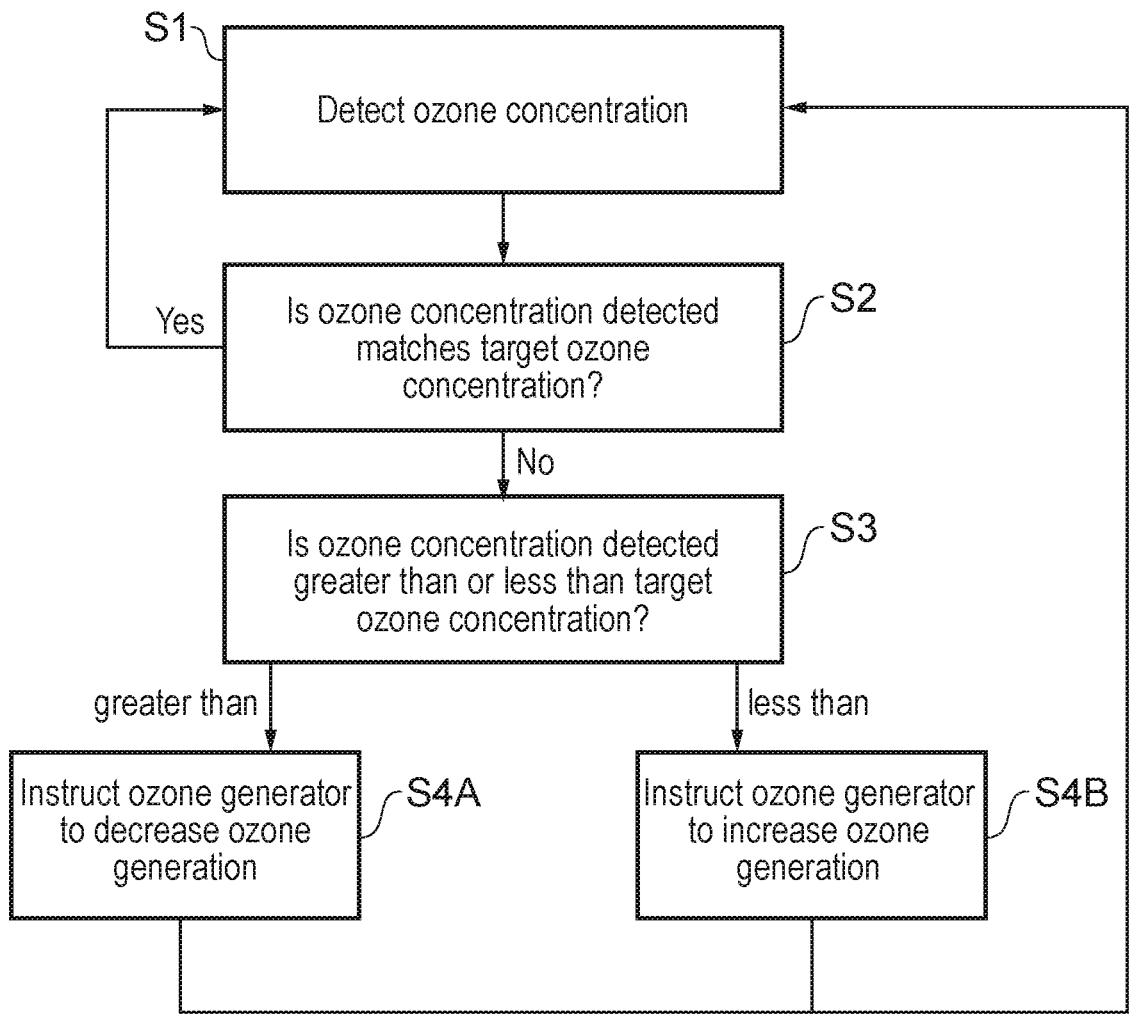
FIG. 12 is a flow chart illustrating a method of detecting ozone in the water purification system illustrated in FIG. 11.

FIG. 12 is a flow chart illustrating a control process used by the processor 112 of the water purification system. This control process can use the detected ozone concentration at the sensor 110 to control the activity of the ozone generator 114. As will be appreciated, under-production of ozone may result in incomplete purification of the water and over-production of ozone may be wasteful of electrical energy used to power the ozone generator.

The control process illustrated in FIG. 12 operates as a loop, and the loop may operate on an entirely continuous basis or may operate with a small delay before the recommencement from step S1 on each performance of the loop. Each performance of the loop commences at step S1, in which the concentration of ozone at a particular point in the system is detected by sensor 110.

Next in step S2, this detected ozone concentration is compared to a target ozone concentration and it is determined if the detected ozone concentration matches a target ozone concentration. In the present example a minimum desired ozone concentration is 0.07 ppm. Excess amounts of ozone are however unnecessary and their generation may incur additional cost and/or waste energy. Thus a maximum desired ozone concentration is 0.08 ppm. The target ozone concentration is therefore 0.07-0.08 ppm. Thus, in step S2 it is determined if the detected ozone concentration is between 0.07 and 0.08 ppm.

If the detected ozone concentration matches the target ozone concentration then the method returns to step S1 in order to continually monitor ozone concentration.

If the detected ozone concentration does not match the target ozone concentration then the method proceeds to step S3 in which it is determined whether the detected ozone concentration is greater or less then the target concentration.

If the detected ozone concentration is greater than the target ozone concentration then at step S4A a signal is sent to the ozone generator 114 to reduce the amount of ozone it generates. The method then returns to step S1 to detect the new ozone concentration after the decrease in ozone generation and the loop continues.

If on the other hand, the detected ozone concentration is less than the desired ozone concentration than a signal is sent at step S4B to the ozone generator 114 to increase the amount of ozone generated thereby increasing the concentration of ozone in the system. The method then returns to step S1 to detect the new ozone concentration after this increase in ozone generation and the loop continues.

In this manner the concentration of ozone in water can be monitored in real time throughout a water purification system and any deviations from the desired level of ozone can be addressed rapidly (with minimal delay) as they occur.

In the ozone sensor described above with reference to FIGS. 1-4, a pipe having a circular cross section is illustrated. However the pipe may be any shape or have any suitable cross section provided it can focus light as it enters the pipe.

As described above the tube through which the fluid flows is formed of a transparent material. However in certain alternative examples the tube is formed of an opaque material having transparent windows located therein in order to allow light to be directed through the tube to the detector. Thus only a portion of the tube may be transparent to light emitted from the source.

In further alternative examples the sensor may be used to detect ozone concentration in water in a container other than in a pipe that allows fluid flow therethrough. In such examples the container acts as a housing for the water. In order to focus the light as it enters the container the container has a suitable cross section arranged to focus light as it enters the container. Typically the surface at which light enters the container will therefore be a curved surface.

In the example ozone sensor described above, the detector is located substantially opposite the source such that light emitted from the source follows a substantially straight path from source to detector. However in alternative examples the detector may be offset from the source and the pipe arranged to focus the light emitted from the source onto the detector such that the optical path between the source and the detector is angled and not a straight line.

Although the detector has been described as being located outside the pipe in the above described example, in some examples the detector is embedded in the pipe. This provides a more compact device which can be beneficial where space is limited.

In the example sensor described above, the pipe is arranged to focus the light emitted from the source in one dimension only. However in alternative examples the pipe may be arranged to focus the light in two dimensions. In such an example a top view of the pipe would also show focussing of the light towards the detector. In a further alternative example the pipe may provide no focussing of the light. This example has particular utility where the source used is arranged to provide a collimated beam output for example a laser source.

In the example described above the detector is provided on the opposite side of the quartz pipe to the photodiode. However it is believed that the detector could be provided on the same side as the photodiode. In such examples the light emitted from the photodiode is reflected off the back of the pipe and detected by a detector located adjacent to the photodiode. For example a reflector or mirror placed behind the pipe is believed to be suitable to achieve the required reflection. In an alternative example it is believed that the outside of the pipe could be silvered on the opposite side to the source and detector in order to provide the required reflection. In a further alternative example a single component combining the functions of emission and detection of light may be provided.

In a further example a pipe that splits into two pipes may be used in conjunction with a single LED and two photodiodes. The LED may be provided before the pipe splits such that it can direct light into both pipes and photodiodes are provided downstream of the LED after the pipe splits such that one photodiode is provided in each pipe. An ozone generator is provided in one pipe after the split such that one pipe contains ozonated water and the other pipe contains water without any ozone present. In this manner the concentration of water before and after ozonation can be monitored using a single LED.

In the example water purification system illustrated in FIG. 12, ozone concentration is detected at a single point after the introduction of ozone by the ozone generator. However in an alternative example, a more complex water purification system such as that illustrated in FIG. 13 can be provided. In the system illustrated in FIG. 13, a plurality of ozone sensors 210*a*, 210*b*, 210*c*, 210*d* are positioned at a plurality of positions throughout the system. Each of the sensors 210*a*, 210*b*, 210*c*, 210*d* is connected to a processor 212 that controls an ozone generator 214. The ozone generator 214 is arranged to introduce ozone into the system at a plurality of locations a, b, c, d depending on where it is detected that ozone is required. The number of ozone introduction locations a, b, c, d is equal to the number of ozone sensors 210*a*, 210*b*, 210*c*, 210*d* and each ozone introduction location a, b, c, d is associated with a particular sensor 210*a*, 210*b*, 210*c*, 210*d*. Thus if it is detected that the ozone concentration detected by sensor 210*b* is lower than a target ozone concentration, the controller 212 controls the ozone generator 214 to introduce ozone at location b. Additionally each of the ozone introduction locations a, b, c, d is positioned at least a distance y upstream of its associated ozone sensor 210*a*, 210*b*, 210*c*, 210*d* as discussed above with respect to FIG. 11.

In a further alternative example, a water purification system includes a plurality of ozone sensors and an equal number of ozone generators. Each ozone generator is associated with a particular ozone sensor and is distanced from the ozone sensor as described earlier with respect to the water purification system illustrated in FIG. 11. A single controller is provided to control the plurality of ozone sensors and ozone generators. The controller is arranged to control a single ozone generator and its corresponding ozone sensor as a single unit such that when it is detected by a particular sensor that an ozone concentration does not meet a target ozone concentration, the controller controls the ozone generator associated with that sensor to increase or decrease the amount of ozone generation according to the method described in FIG. 12.

Although in the examples described above an equal number of ozone sensors and ozone generators (or locations for the introduction of ozone) are provided, it will be appreciated that the present disclosure is not limited solely to examples in which an equal number of zone sensors and ozone generators are provided. In further alternative examples a different number of ozone sensors to ozone generators may be provided. In one example there may be two ozone sensors per ozone generator. In such an example one ozone sensor may be located upstream of the ozone generator the output of which is used to determine if and how much ozone should be introduced to the system. A second ozone sensor may be located downstream of the ozone generator and may be used to determine whether the increase or decrease of ozone in the system has resulted in the target concentration. In other examples a plurality of ozone sensors are provide throughout the system but ozone may only be introduced into the system at one location. Thus the present disclosure is not limited to a particular number of ozone sensors or ozone generators or to a particular relationship between the number of ozone sensors and the number of ozone generators.

In the method of controlling ozone concentration described with reference to FIG. 12, the method immediately returns to step S1 upon either determining that the detected ozone concentration matches the target ozone concentration S2 or upon instructing the ozone generator to increase or decrease ozone generation S4A, S4B. However in some examples the frequency of ozone detection is reduced such that a delay is introduced before the method returns to step S1. In these examples an additional step of waiting for a period of time e.g. 30 seconds is introduced before the method returns to step S1.

Figure 13:
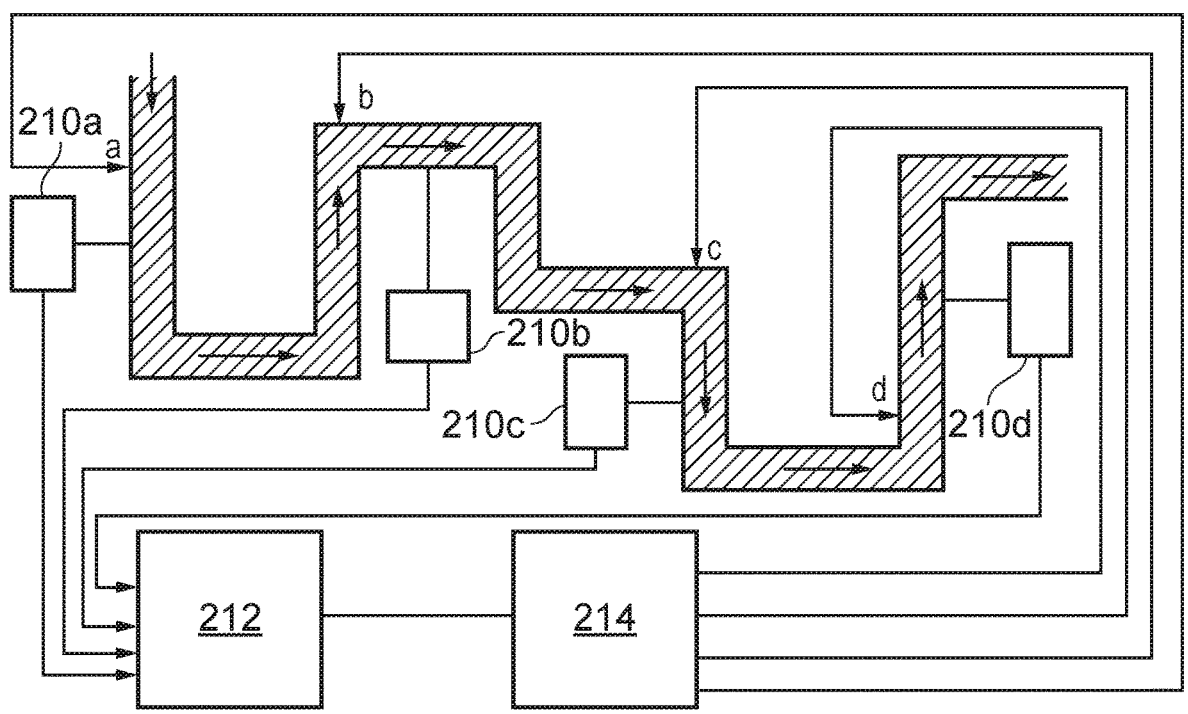
FIG. 13 illustrates an alternative water purification system including a plurality of sensors illustrated in FIG. 1.

In the examples described with respect to FIGS. 11-13 a signal is sent to an ozone generator to increase or decrease the amount of ozone generated as soon as a difference between the desired and detected ozone concentrations is determined. However in some examples the signal may only be sent to the ozone generator if a difference between the desired and detected ozone concentrations is present for a predetermined period of time. In such an example the water purification system includes an additional step of monitoring the ozone concentration for a period of time once it has been determined that the ozone concentration does not match the target ozone concentration at step S2. Once the period of time has elapsed, if the ozone concentration has not matched the target concentration for the duration of that time, then the method proceeds to step S3. If instead the ozone concentration has matched the target concentration during the period of time then the method returns to step S1.

Although in the discussion above only the detection of ozone has been described. It will be appreciated that the sensor of the present disclosure may also be used to detect other substances in water and indeed in other fluids by using the emission absorption and detection of different wavelengths of light depending on the substance to be detected and the fluid in which it is located. For example the sensor may be used to detect metals or metal oxides such as iron, iron oxide or manganese in water. These materials are undesirable in water and therefore may be considered to be negative substances which should be reduced or removed. In contrast it is desirable for ozone to be present in water since ozone is able to remove impurities and deactivate biological substances, for example protozoa. As such ozone may be considered to be a positive substance the presence of which is advantageous.

Whilst in the examples described above a single range of wavelengths has been used to detect the concentration of a particular substance, in some examples multiple wavelength ranges may be used to detect the concentration of a substance. For example absorption of light of wavelength Z could indicate the presence of either substance A or substance B and absorption of light of wavelength Y could indicate the presence of either substance B or substance C. The absorption of wavelength Y can be subtracted from the absorption of wavelength Z in order to give the concentration of (A-C). If is known that substance C is not present then the concentration of substance A has been calculated from the absorption of different wavelengths of light. In this manner the concentration of a variety of different substances may be detected by combining the measurements of absorption of different wavelength of light.

The detection of manganese in water is one example where the absorption of light at multiple wavelengths may be used. Measurement of absorption of light at wavelengths of 450 nm and 700 nm is believed to be suitable to detect the concentration of manganese. Similarly the detection of iron in water may also utilise absorption at multiple wavelengths. Detecting the absorption of light at wavelengths of 250 nm and 400 nm is believed to be suitable for the detection of iron in water. In some examples absorption at different wavelengths may be carried out simultaneously using a white LED and a linear detector array. In other examples multiple LEDs may be used with each LED emitting a certain wavelength.

It is believed that sensors for detecting the concentration of iron and manganese may also be used in the water purification systems described with reference to FIGS. 11-13. The following example discusses the detection of iron but the method and apparatus could be equally applicable to detecting manganese in a water purification system.

At least one sensor for detecting iron may be provided in the water purification system of FIG. 11 in place of the ozone sensor and at least one concentration mitigation device may be provided in place of the ozone generator. In the present example therefore the controller may be provided to control the concentration mitigation device in dependence upon the concentration of iron detected by the iron sensor. The arrangement of the at least one sensor and the at least one concentration mitigation device may be the same as the arrangement of the ozone sensor(s) and ozone generator(s) in the water purification systems described with reference to FIGS. 11-13. The distance between the sensor and the concentration mitigation device may be set in dependence upon the flow rate of water in the manner described above.

When it is detected that the concentration of the iron does not match the target concentration the use of the concentration mitigation device (instead of an ozone generator as described above) may be increased or decreased depending on whether the concentration of the substance is too high or too low. Examples of concentration mitigation devices may include a device arranged to introduce a reagent to the water that enables the precipitation of iron out of the water or alternatively a device arranged to introduce a dilutant into the water such that the concentration of the iron is reduced. In another example a waste material discharge gate may be arranged to reduce the iron flow rate. Thus a concentration mitigation device may also be considered to be a concentration modifier or adjuster that enables adjustment of a concentration of iron in a fluid. As discussed above it is believed that a similar system would be suitable to control the concentration of manganese using a manganese sensor. Thus water purification systems arranged to control the concentration of undesirable or negative substances such as iron and manganese also form part of the present disclosure.

In the above described examples the use of one type of sensor to detect for example ozone or iron in a water purification system has been described. However in some examples, a water purification system may include different types of sensors at different locations in the system depending on where an apparatus for removing or introducing a particular substance is located. For example an iron concentration sensor and iron removal apparatus may be provided upstream and an ozone concentration sensor and ozone generator may be provided downstream. It will be appreciated that any combination of sensors and associated concentration modifiers may be used in conjunction with one another depending on the substances to be detected and removed.

Although the detection of different substances in water has been described, it is believed that the apparatus described is also suitable for the detection of substances in fluids other than water. The apparatus described is therefore not solely limited to the detection of substances in water but may also be used to detect substances in any suitable fluid. For example the present sensor may be deployed to detect positive or negative substances in hydrocarbon fuels e.g. petrol, diesel or oil. In one particular example the present approach may be deployed for detecting the presence of the negative substances iron, zinc or sulphur in petrol. The approach of the present disclosure may also be deployed to detect the presence of certain substances in gases. One example of such potential use is to detect the presence of carbon monoxide in exhaust gases. The apparatus may also be suitable for the detection of substances in other fluids for example acids or alcohols.

Thus an apparatus and method for detecting the concentration of a substance in a fluid that allows detection of a substance to be made in situ, in real time, has been described. In some examples the apparatus includes a housing arranged to contain the fluid, a source operable to generate and direct light through the housing containing the fluid, wherein the housing is configured to focus light passing therethrough; and a detector operable to detect the intensity of light transmitted through the housing.

An apparatus and method for controlling the concentration of a substance in a fluid has also been described. In some examples the apparatus includes a sensor of the type described above arranged to detect a substance concentration of a system, a comparator arranged to compare a detected substance concentration with a target substance concentration, and a substance concentration adjuster arranged to alter the concentration of the substance in the system when a detected substance concentration does not match the target substance concentration.

The methods and apparatuses described have been shown to be applicable to a wide range of applications and are not limited to the specific examples described. The scope of the present disclosure is therefore defined by, and includes any alternatives or modifications that fall within, the spirit and scope of the appended claims.

The invention claimed is:

1. An apparatus for detecting a concentration of one or more substances in a fluid, the apparatus comprising:
    a housing arranged to contain the fluid;
    a source operable to generate and direct light through the housing, wherein the housing is configured to focus light passing therethrough; and
    a detector operable to detect an intensity of light transmitted through the housing,
    wherein a distance between the source and the detector is selectively adjustable in dependence upon a substance of the one or more substances to be detected and a wavelength of the light generated by the source.

2. An apparatus according to claim 1, wherein the housing is arranged to permit a substance of the one or more substances in the fluid in the housing to absorb a proportion of light emitted from the source before it is detected by the detector.

3. An apparatus according to claim 1, wherein the detector comprises a photosensitive element arranged to produce a signal responsive to the intensity of the light transmitted through the housing and received by the detector.

4. An apparatus according to claim 3, wherein the signal is an indicator of a quantity of the one or more substances in the fluid in the housing.

5. An apparatus according to claim 1, wherein a portion of the housing is transparent to light emitted from the source.

6. An apparatus according to claim 1, wherein the detector is positioned proximate to the housing and in an optical path of light from the source that has passed through the housing.

7. An apparatus according to claim 1, wherein the wavelength of the light generated by the source is selected in dependence upon a substance of the one or more substances to be detected and the fluid containing the substance of the one or more substances.

8. An apparatus according to claim 1, wherein the housing comprises a focussing structure arranged to focus light incident on the focussing structure.

9. An apparatus according to claim 8, wherein the focussing structure is arranged to focus light as the light enters the housing.

10. An apparatus according to claim 8 wherein the focusing structure is arranged to focus light as the light exits the housing.

11. An apparatus according to claim 8, wherein the source is positioned proximate to the housing, and wherein the source is arranged to direct light to the focussing structure, through the housing.

12. An apparatus according to claim 1, wherein the housing comprises a hollow member connectable to a fluid flow so as to permit fluid flow therethrough.

13. An apparatus according to claim 12, wherein the hollow member comprises a focussing structure arranged to focus light incident on the focussing structure, and wherein the focussing structure is a part of a shape of the hollow member.

14. An apparatus according to claim 13, wherein the focussing structure comprises at least one curved surface of the hollow member.

15. An apparatus according to claim 12, wherein the hollow member is in a form of a tube.

16. An apparatus according to claim 12, wherein the hollow member has a circular cross-sectional area.

17. An apparatus according to claim 1, wherein the housing comprises at least one connector arranged to connect the housing to pipes for fluid flow.

18. An apparatus according to claim 1, wherein the detector is embedded in the housing.

19. An apparatus according to claim 1, further comprising a lens provided between the source and the housing, and arranged with a position to focus light emitted from the source before the light enters the housing.

20. An apparatus according to claim 1, wherein the source is a light emitting diode (LED).

21. An apparatus according to claim 20, wherein the LED comprises a hemispherical lens arranged to focus the light before the light enters the housing.

22. An apparatus according to claim 1, wherein the source is a laser.

23. An apparatus according to claim 1, wherein the housing is formed of quartz.

24. An apparatus according to claim 1, wherein the apparatus is arranged to detect a concentration of a substance of the one or more substances in water.

25. An apparatus according to claim 24, wherein the apparatus is arranged to detect a concentration of a positive substance of the one or more substances in water.

26. An apparatus according to claim 25, wherein the positive substance comprises ozone.

27. An apparatus according to claim 1, wherein the apparatus is arranged to detect a concentration of a negative substance of the one or more substances in water.

28. An apparatus according to claim 27, wherein the negative substance comprises manganese or iron.

29. A method of detecting a concentration of of one or more substances in a fluid, the method comprising:
    directing light from a source through a housing containing fluid, wherein the housing is arranged to focus the light passing therethrough;
    detecting an intensity of light transmitted through the housing using a detector; and
    selectively adjusting a distance between the source and the detector depending on a substance of the one or more substances to be detected and a wavelength of light from the source.

30. A method according to claim 29, wherein the housing is arranged to permit a substance of the one or more substances in the fluid in the housing to absorb a proportion of light emitted from the source before it is detected.

31. A method according to claim 29, the method comprising producing a signal responsive to the intensity of the light transmitted through the housing.

32. A method according to claim 31, wherein the signal is proportional to a quantity of the one or more substances in the fluid in the housing.

33. A method according to claim 29, the method comprising positioning the detector proximate to the housing and in an optical path of light from the source that has passed through the housing.

34. A method according to claim 29, wherein the housing comprises a focussing structure arranged to focus light incident on the focussing structure.

35. A method according to claim 34, comprising positioning the source proximate to the housing, and directing the light from the source to the focussing structure and through the housing.

36. A method according to claim 34, comprising using a part of a shape of the housing as the focussing structure.

37. A method according to claim 29, comprising directing the light from the source through a lens before the light passes through the housing containing the fluid.

* * * * *